US008298784B2

(12) United States Patent  
Bergmann et al.

(10) Patent No.: US 8,298,784 B2  
(45) Date of Patent: Oct. 30, 2012

(54) IN VITRO PROCEDURE FOR DIAGNOSIS AND EARLY DIAGNOSIS OF NEURODEGENERATIVE DISEASES

(75) Inventors: Andreas Bergmann, Berlin (DE); Andrea Ernst, Henningsdorf (DE); Harald Hampel, München (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

(21) Appl. No.: 12/300,747

(22) PCT Filed: May 15, 2007

(86) PCT No.: PCT/EP2007/004314
§ 371 (c)(1),
(2), (4) Date: Mar. 13, 2009

(87) PCT Pub. No.: WO2007/131775
PCT Pub. Date: Nov. 22, 2007

(65) Prior Publication Data
US 2009/0263822 A1 Oct. 22, 2009

(30) Foreign Application Priority Data

May 17, 2006 (DE) .......................... 10 2006 023 175

(51) Int. Cl.
*G01N 33/53* (2006.01)
*G01N 33/537* (2006.01)
*G01N 33/567* (2006.01)

(52) U.S. Cl. ........ 435/7.8; 435/7.1; 435/7.21; 435/7.92; 435/7.93; 436/503

(58) Field of Classification Search .................. None
See application file for complete search history.

(56) References Cited

U.S. PATENT DOCUMENTS

2006/0234295 A1 10/2006 Bergmann et al.

FOREIGN PATENT DOCUMENTS

| JP | 06160383 | 6/1994 |
| WO | 2004/046181 | 6/2004 |
| WO | 2004/059293 | 7/2004 |

OTHER PUBLICATIONS

Silver, 2006, Current Opinion in Nephrology and Hypertension, 15, pp. 14-21.*
Mukadeeam-Daher, 2006, Expert Opin. Ther. Targets, 10, (2), pp. 239-252.*
Daniels et al., 2006, Heart Failure Clin. 2, pp. 299-309.*
Dietz, 2005, Cardiovascular Res., 68, pp. 8-17.*
Reisberg, Barry et al., "The Global Deterioration Scale for Assessment of Primary Degenerative Dementia", Am J Psychiatry 139:9, Sep. 1982; 1136-1139.
McKhann, Guy et al., "Clinical Diagnosis of Alzheimer's disease: Report of the NINCDS-ADRDA Work Group* Under the Auspices of Department of Health and Human Services Task Force on Alzheimer's Disease", Neurology 34, Jul. 1984; 939-944.
McKeith, Ian G., "Dementia with Lewy Bodies", British Journal of Psychiatry, (2002), 180, 144-147.
Frank, Richard A. et al., "Biological Markers for Therapeutic trials in Alzheimer's disease. Proceedings of the biological markers working group; NIA initiative on neuroimaging in Alzheimer's disease", Neurobiology of Aging 24, (2003), 521-536.
Growdon J.H., et al., Consensus Report of the Working Group on: "Molecular and Biochemical Markers of Alzheimer's Disease", (Working Group Advisory Committee) (1998) [Ronald and Nancy Reagan Research Institute of the Alzheimer's Association and the National Institute on Aging Working Group on Biological Biomarkers of Alzheimer's Disease]. Neurobiology of Aging, vol. 19(2), 109-116.
Morgenthaler, Nils G., et al., "Immunoluminometric Assay for the Midregion of Pro-Atrial Natriuretic Peptide in Human Plasma", Clinical Chemistry 50, No. 1, 2004, S. 234-236.
Teunissen C.E. et al., "Biochemical markers related to Alzheimer's dementia in serum and cerebrospinal fluid", Neurobiology of Aging 23 (2002): 485-508.
Tarkowski Elisabeth, "Cytokines in Dementias", Current Drug Targets—Inflammation & Allergy, 2002; vol. 1(2), 193-200.
Tarkowski Elisabeth, et al., "Cerebral pattern of pro-and anti-inflammatory cytokines in dementias", Brain Research Bulletin 61 (2003) 255-260.
Chu, Duc Quyen et al., "Studies of the microvascular effects of adrenomedullin and related peptides", Peptides 22 (2001), 1881-1886.
Nilsson Karin et al., "Plasma Homocysteine Concentration and Its Relation to Symptoms of Vascular Disease in Psychogeriatric Patients", Dement Geriatr Cogn Disorder 2005: 20:35-41.
Muders Frank, MD., et al., "Evaluation of plasma natriuretic peptides as markers for left ventricular dysfunction", American Heart Journal, Sep. 1997, vol. 134(3), 442-449.
International Search Report (German) for corresponding PCT/EP2007/004314.
Albadalejo M D., et al: "Plasmatic determination of natriuretic peptides in demented patients", Revista De Neurologia, Mar. 1997, Bd. 25, Nr. 139, Mar. 1997.

* cited by examiner

*Primary Examiner* — Olga N Chernyshev
(74) *Attorney, Agent, or Firm* — Heslin Rothenberg Farley & Mesiti P.C.

(57) ABSTRACT

An in vitro process for the detection and early detection of neurodegenerative diseases, for determination of the severity, and to evaluate the progression of and render a prognoses of neurogenerative diseases, in a patient suffering from a subjectively or objectively detectable cognitive impairment, by determining the concentration of an analyte selected from natriuretic peptides, in particular ANP, and, if necessary, BNP and/or CNP in a biological fluid of the patient, whereby the determination of the analyte is performed directly and/or indirectly as the determination of a relevant co-peptide generated from a mutual propeptide, and is based upon the measured concentration of the determined analyte thus making it possible to form conclusions about a neurodegenerative disease or an early form typical of such a disease or the course of the disease and/or the success of the efforts to relieve or prevent the disease.

4 Claims, 1 Drawing Sheet

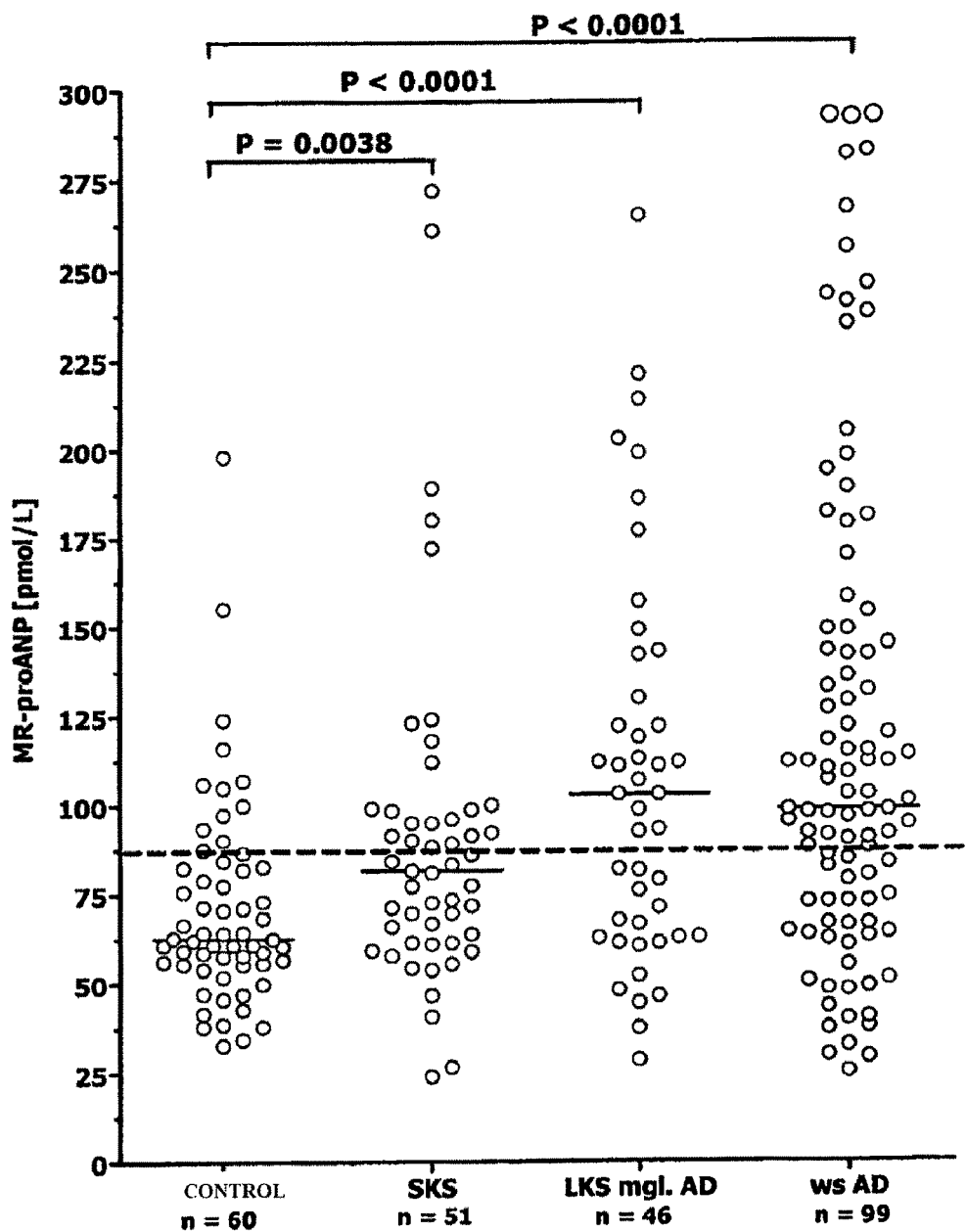

IN VITRO PROCEDURE FOR DIAGNOSIS AND EARLY DIAGNOSIS OF NEURODEGENERATIVE DISEASES

CROSS REFERENCE TO RELATED APPLICATIONS

This application is a 371 filing of PCT International application no. PCT/EP2007/004314 filed May 15, 2007 and published in German as WO 2007/131775 A1 on Nov. 22, 2007, which claims the priority of German application no. 102006023175.9 filed May 17, 2006. The disclosures of these applications and all other patents, published applications and other references cited herein are hereby incorporated by reference in their entirety.

The present invention relates to a novel in vitro method for the diagnosis and in particular early diagnosis of neurodegenerative diseases, in particular of dementias, such as Alzheimer's disease and precursors thereof.

In the context of the present invention, the term "diagnosis" is used as an overall term for medical determinations which may be based on different problems according to the clinical condition of the patient for whom the determination is carried out and which serve for the detection and, in the present case, in particular also for the early detection, the determination of the severity and the assessment of the course, including the therapy-accompanying assessment of the course, and the prognosis of the future course of a disease. What is of particular importance in the present context is that a diagnosis may also be a negative diagnosis in which the presence of a certain disease is made improbable owing to the failure to establish a certain feature typical of the disease, for example the nondetectability of a biomarker associated with the relevant disease in a blood sample of a patient.

Biomarkers which can be found at elevated levels in the case of a plurality of different diseases and therefore by themselves do not permit a positive diagnosis of a specific disease—although as a rule they may also be decisive for the positive diagnosis on inclusion of further clinical or biochemical parameters—and of also great value for the negative diagnosis.

The diseases regarding the diagnosis of which the present invention is concerned tend to be slowly developing, chronic neurodegenerative diseases of noninfectious etiology, in particular presenile dementias.

Dementias are designated generally as diseases for which a common feature is the loss of acquired intellectual abilities, especially of memory, and of the normal developing diseases of chronic character. If dementias occur prior to old age, in middle age, they are referred to as presenile dementias and they are differentiated on the basis of the symptoms and cerebropathological changes typical of them, in particular the following diseases or groups of diseases:

Alzheimer's disease (AD) is the most frequent neurodegenerative dementia, accounts for ⅔ of all cases of dementia and is also the practically most important field of use for the present invention. AD is distinguished by three important pathological features which however can be detected with certainty only post mortem: the formation of amyloid plaques and neurofibrillar bundles and the loss of nerve cells (for an overview cf. (1); literature references in the description in the form of numbers relate to the list of references following the description). Amyloid plaques consist of extraneuronal aggregates of the amyloid-β protein, while the neurofibrillar bundles contain mainly tau-protein and neurofilaments. It is presumed that the plaque and neurofibril formation is the cause of the death of nerve cells.

The most important symptoms of AD are increasing impairment of the capacity to register and disturbance of intellectual function in combination with relatively persistent emotional responsiveness, these symptoms being accompanied by further less specific disturbances which make it more difficult to distinguish AD from other forms of dementia.

Observations of AD patients and patients who develop AD in the course of their clinical observation over many years led to the formulation of criteria for mutually distinguishable groups of patients which cover the entire range of (a) persons without subjective and objective cognitive disturbances (which in the context of the present invention represent the control group) through (b) patients who complain about subjective diminished cognitive ability but in whom no cognitive deficits can be found (in the context of the present invention, this is the group of "SCD" patients, where "SCD" represents "subjective cognitive disturbances"), further through (c) patients who have been found to have mild cognitive disturbances and who have been diagnosed with "possible AD" ("pos AD") where no other dementia-causing diseases are present (in the context of the present invention, this is the group "MCD pos AD", where "MCD" represents "mild cognitive disturbances") to (d) the group of patients with the typical clinical picture for considerable cognitive disturbances which have begun gradually and progress slowly, which patients are diagnosed with "probable AD" when other causes of dementia can be ruled out (in the context of the present invention, this is the group "pr AD", where the abbreviation represents "probable Alzheimer's").

Regarding the assignment of patients with subjective and/or objective cognitive disturbances to various groups, reference is additionally made to (2), (3), (4) and (5).

Dementia with lewy bodies (DLB) is the second most frequent cause of a dementia after Alzheimer's disease. Neuropathologically, DLB is characterized by the occurrence of so-called lewy bodies in the brain stem and in the cortex. These lewy bodies predominantly comprise aggregates of the presynaptic protein (α-synuclein) and ubiquitin. The lewy body pathology can be associated to various extents with Alzheimer- and Parkinson-typical neuropathological changes. Thus, in the case of DLB too, the formation of beta-amyloid and senile plaques occurs, but not neurofibril bundles (for an overview, cf. (6)). Lewy bodies are also present in the brain of patients with Parkinson's disease, although in a different distribution.

The key symptoms of DLB are a progressive cognitive disturbance, episodes of confusion with fluctuating attentiveness and awareness, Parkinsonism, frequent falls and syncopes (brief, paroxysmal unconsciousness). The sensitivity and specificity of the diagnostic criteria show high specificity throughout but in some cases very low sensitivity. This means that DLB is frequently not diagnosed in day-to-day clinical routine.

Frontotemporal dementia (FTD) is also referred to as Pick's disease and accounts for about 20% of presenile dementias. FTD is in some cases of genetic origin and is among the so-called tauopathies, which are distinguished by overexpression or underexpression of a tau-protein subtype or by the expression of a mutated tau-protein. Neuropathologically, local atrophy of the frontal and/or temporal cortex and of the substantia nigra and of the basal ganglia occurs. This results in speech disturbances of varying severity, a personality change and behavioral abnormalities. Overall, FTD is underdiagnosed with a sensitivity of 93% and a specificity of only 23%, AD representing the most frequent misdiagnosis.

The term vascular dementia (VAD) summarizes diseases in which a dementia is triggered owing to blood flow disturbances in the brain. There are different types of VAD, of which multi-infarction dementia (MID) and subcortical VAD (also referred to as Binswanger's disease) are the most frequent forms.

Binswanger's disease is a slowly progressing dementia which is characterized pathologically by cerebrovascular lesions in the white brain substance. Clinically, this results in behavioral abnormalities, such as agitation, irritability, depression and euphoria, and slightly impaired memory.

Multi-infarction dementia occurs gradually as a result of a plurality of small strokes, also referred to as transient ischemic attacks (TIA), which led to the destruction of brain tissue in the cortex and/or subcortical areas. The strokes may also have remained completely unnoticed, in which case the dementia is the first noticeable consequence. When MID is present, there is a gradual decrease in cognitive abilities, associated with severe depressions, mood variations and epilepsy.

A diagnosis of dementia is carried out nowadays predominantly on the basis of neuropsychological investigations and observation of the development of the disease and its course, using exclusion criteria for certain forms of dementia. In very many cases, these investigations give ambiguous results, which explain the abovementioned numbers for the underdiagnosed forms of dementia or incorrectly diagnosed cases. The cerebral changes typical of the disease cannot of course be determined directly on living patients, example, X-ray tomography or magnetic resonance imaging are complicated and expensive.

It would therefore be desirable to be able to supplement and thereby considerably improve the detection and in particular early detection of dementias by the measurement of informative biomarkers which can be determined, for example, in a blood sample (serum sample, plasma sample) of a patient with the aid of a relatively simple test method.

For the diagnosis of Alzheimer's disease, the Ronald and Nancy Reagan Institute of the Alzheimer's Association and the NIA Working Group published guidelines for the criteria which are set regarding an ideal biomarker for the detection of AD (7). The following criteria should ideally be fulfilled by the biomarker:

1. It should be brain-specific and detect a fundamental feature of the neuropathology of these diseases.
2. The diagnostic sensitivity and the specificity of at least 80% should exist.
3. The disease-specific change of the biomarker should manifest itself in as early a stage as possible of the disease, in order to be able to begin suitable therapeutic measures (8).

Up to the present, however, there is no biomarker which could be used in day-to-day clinical routine in the blood or the cerebrospinal fluid with sufficient certainty for the early and differential diagnosis of AD and fulfills all abovementioned criteria. At present, various potential marker candidates are being investigated, including inflammation markers, such as IL-6 and TNFα, markers for oxidative stress, such as 3-nitrotyrosine, and markers which are associated with characteristic pathological changes of AD, such as amyloid β, which is a main constituent of the amyloid plaques, and the tau-protein, which is a substantial constituent of the neurofibril bundles (cf. the overview in (7); (10)).

There is a current demand for supplementary investigative methods which provide valid laboratory findings and which are based on a determination of substances suitable as biomarkers for dementias, in particular for Alzheimer's disease (AD), in blood or plasma samples and are suitable for supporting an early positive diagnosis and/or for a negative diagnosis by exclusion in the case of patients who are suspected of having a dementia, in particular AD.

The present invention provides such an investigative method in the form of an in vitro method for the detection and early detection, for the determination of the severity and for the assessment of the course and prognosis of neurodegenerative diseases, in which the concentration of an analyte which is selected from the natriuretic peptides is determined in a biological fluid of a patient who is suffering from subjective or objectively detectable cognitive disturbances, it being possible to effect the determination of the analyte directly and/or indirectly via the determination of an associated copeptide formed from a common propeptide, and in which conclusions regarding the presence of a neurodegenerative disease or an early form thereof typical of said disease or regarding the course of the disease and/or the success of the efforts to alleviate or prevent it are drawn on the basis of the measured concentration of the analyte determined.

Advantageous or preferred developments of a method according to claim 1 are described in subclaims 2 to 10.

The peptides ANP (the "atrial-natriuretic peptide"), whose determination is preferably effected in the form of the determination of so-called NT-proANP (of N-terminal pro-ANP, i.e. of the N-terminal partial peptide which is formed on release of ANP from the common precursor), BNP (of the so-called "brain-natriuretic peptide"), whose determination is likewise effected in the form of the determination of so-called NT-proBNP (of N-terminal pro-BNP, i.e. of the N-terminal partial peptide which is formed on release of BNP from the common precursor), and the related so-called CNP, which has the shortest peptide chain of said natriuretic peptides, may be regarded in particular as "natriuretic peptides or copeptides thereof formed from a common propeptide".

In the context of the present invention, ANP is preferably determined, in particular preferably as MR-proANP, while the determination of NT-proANP is effected preferably with the aid of an immunoassay which detects the amino acid sequences in the midregional area (MR) of proANP or NT-proANP and which is described in more detail in WO 2004/046181 or European patent EP 1 562 984 B1 arising therefrom. A further description of this immunoassay is to be found in (9).

A preferred variant of the method according to the invention consists in determining not only a natriuretic peptide alone but, in addition to the determination of ANP, which is preferably effected by the abovementioned assay method, also determining BNP by any known method for the direct or indirect determination of BNP and to consider the results of the measurements for the determination of ANP and BNP together, usually by simultaneously taking into account the clinical findings and other test parameters for the respective patients, and to use them for the evaluation.

The present invention is based on considerations by the inventors to improve the diagnosis of dementia diseases by making use of the knowledge that the known forms of presenile dementia which were explained in more detail at the outset are also accompanied—to different extents—by inflammatory processes and endothelial damage, which are regarded as essential for the development, the symptoms and the course of the dementias, and it is for this reason that neurodegenerative diseases can also be regarded as neuroinflammatory diseases.

Thus, Alzheimer's disease is characterized, inter alia, by the occurrence of chronic local inflammatory reactions in the brain with participation of various inflammatory proteins, such as complement factors, acute phase proteins and proinflammatory cytokines (10).

Inflammatory processes also play a role in the origin of vascular dementias (VAD). The levels of TNFα, TGFβ, IL-6 and GM-CSF (granulocyte-macrophage stimulating factor) are substantially increased in patients with VAD (11, 12).

In the case of DLB, too, inflammatory processes appear to play a role. Thus, the number of activated microglia cells in the brain of patients with DLB is increased, and proinflammatory cytokines, such as TNFα, are overexpressed in certain brain regions, such as the amygdala and the hippocampus.

On the other hand, there is only information in isolated cases regarding the occurrence of inflammatory reactions in the brain of FTD patients.

Starting (i) from the hypothesis that the neuroinflammatory processes associated with dementias lead to blood flow disturbances, in particular to microcirculation disturbances of the brain, and (ii) that to this extent there is a similarity with cardiovascular diseases which are associated with blood flow disturbances or disturbances of the microcirculation (13) of the heart tissue, and (iii) from analytical findings which show that increased formation, inter alia, of the natriuretic peptides ANP and BNP is detectable in the case of such cardiovascular diseases, and finally (iV) using the improved analytical possibilities for the determination of the natriuretic peptide in reliable and in clinically valid form with aid of the abovementioned novel immunoassay of the applicant for determining the midregion of proANP (MR-proANP) according to (9), the inventors investigated the question as to whether indications of elevated concentrations of ANP can also be found in the plasma in the case of patients with different extents of cognitive disturbances, who have otherwise suffered from no known disease associated with increased production of natriuretic peptides.

Where attempts to measure natriuretic peptides in persons who showed dementia-like symptoms were described in the literature, no significant correlation had been found (14, 15).

The measured results, described below in the experimental section, in EDTA plasma samples of apparently 106 healthy normal persons (symptom-free controls) and 196 patients with mild to severe cognitive disturbances according to the groups (b) to (d) described at the outset gave for the first time a clear, diagnostically significant correlation between the concentrations found for MR-proANP and the severity of the dementia symptoms in the form of cognitive disturbances, the measured concentrations correlating in a significant manner with the severity of the disturbances and hence AD precursors and thus contributing to the differentiation of the various patient groups.

Although the investigations were limited to date to plasma samples of patients who showed signs of precursors of AD or who had been diagnosed with "probably Alzheimer's disease", the inventors assume that—possible with different typical concentration ranges—characteristic increases in the MR-proANP concentrations in patient plasmas could be detectable also in the case of other neuroinflammatory forms of dementia, in particular in the case of vascular dementia (VAD and dementia with lewy bodies (DLB)).

The assay method used for the measurements described in the experimental section for MR-proANP in patient plasmas was effected using the abovementioned noncompetitive immunoluminometric sandwich assay (B.R.A.H.M.S SERISTRA®), which is described in more detail in WO 2004/046181 of the applicant or in (9). Reference is expressly made to the general statements on the problems of ANP determination in patient samples and the explanations for carrying out the assay in said publications, for supplementing the statements in the present application.

Below, the invention is explained in more detail with reference to measured results and a FIGURE.

FIG. 1 shows the results of the measurement of the MR-proANP concentrations in EDTA plasmas of 106 healthy control persons and of 196 patients with cognitive disturbances of various severities, who corresponded to the abovementioned groups (b), (c), (d), i.e. the groups "SCD" (50 patients), "MCD pos AD" (46 patients) and "pr AD" (100 patients).

EXPERIMENTAL SECTION

Assay Description

The measurement of MR-proANP is plasma was effected using in immunoluminometric sandwich assay substantially as described in the experimental section of the abovementioned WO 2004/046181 or in (9).

In particular, 10 µl of sample/calibrator and 200 µl of tracer (marked first antibody) were introduced into the tubes coated with the second antibody and incubated for two hours at room temperature (18-24° C.) with mixing (170-300 rpm). Thereafter, the liquid phase was decanted and the tubes were washed four times with 1 ml of LUMItest wash solution (B.R.A.H.M.S Aktiengesellshaft, Hennigsdorf, Germany). The bound chemiluminescence was then measured for 1 s per tube using an LB952T luminometer (Berthold, Wildbad, Germany).

Measurement of MR-proANP in the Plasma of Healthy Controls and Patients with Cognitive Disturbances of Various Severities.

For determining a reference value for the concentration of MR-proANP, a measurement was carried out in EDTA plasmas of 106 symptom-free control persons who neither showed symptoms of cognitive disturbances nor suffered from any other detectable disease (cardiovascular diseases; severe infection or inflammation), for whom it is known that elevated levels of the natriuretic peptides ANP and BNP can be measured in them. For the control group, a median value of 63.45 pmol/l was determined for the measured MR-proANP concentration.

Patients with dementia symptoms in the form of cognitive disturbances of various severities, on the basis of which an assignment of the individual patients was made to one of the abovementioned groups (B), (C) or (d), served as a patient group.

The measured MR-proANP concentrations in the plasma of healthy controls and patients with cognitive disturbances are shown in FIG. 1.

The numerical values determined in the form of the so-called medians for the various patient groups and the specificities and sensitivities for the various patient groups calculated from the measured data using the given value for the cut-off of 80.70 pmol/l were as follows:

|  | Median Controls | Median SCD | Median MCD pos AD | Median Pr AD |
|---|---|---|---|---|
| MR-proANP (data in pmol/l) | 62.6 | 81.5 | 103.0 | 98.8 |

-continued

|  | Cut off (pmol/l) | Specificity (%) | Sensitivity SCD (%) | Sensitivity MCD pos AD (%) | Sensitivity pr AD (%) |
|---|---|---|---|---|---|
| MR-proANP | 87.0 | 81.7 | 43.1 | 58.7 | 64.7 |

The MR-proANP concentrations, evident from the values for the medians of the various patient groups, clearly increase with the severity of the symptoms in the direction:

Controls<SCD<MCD pos AD≈pr AD

Preliminary exploratory determinations of the concentrations of BNP (using a commercial NT-proBNP kit from Roche Diagnostics) in the case of patients from the same patient groups gave sensitivities of 38.0% for the SCD group, 58.0% for the "MCD pos AD" group and 61.0% for the "pr AD" group at a specificity of 82.2%.

The measurement of BNP thus substantially confirms the finding of the measurements of ANP (as MR-proANP). Since it is known that the significance of determinations is as a rule improved in such a situation if more than one parameter is measured and the results of both measurements are considered together for the valuation and/or are combined computationally as suitable manner, the joint determination of ANP and BNP and/or optionally CNP is expressly within the scope of the present invention.

Although increased release of natriuretic peptides, for example of ANP, measured as MR-proANP concentration in a plasma, is also measurable in the case of other diseases (sepsis; cardiovascular diseases/cardiac insufficiency; however these can as a rule be easily differentiated from dementias) and natriuretic peptides are therefore not brain-specific parameters, the ANP determination, optionally in combination with a BNP and/or a CNP determination, is very suitable for purposes of supportive early AD diagnosis, on the basis of the high specificity and the clearly differentiatable sensitivities.

REFERENCES

1. SELKOE D. J. (2001). Alzheimer's disease: genes, proteins, and therapy. Physiological Reviews 81: 741-766
2. Boetsch T., Stübner S. Auer S., Klinisches Bild, Verlauf und Prognose, Chapter 5 in: Hampel, Padberg, Möller (editors), Alzheimer Demenz—Klinische Verläufe, diagnostische Möglichkeiten, moderne Therapiestrategien; WVG mbH Stuttgart 2003
3. Boetsch T., Operationalisierte Demenzdiagnostik, Chapter 6.1 in: Hampel, Padberg, Möller (editors), Alzheimer Demenz—Klinische Verläufe, diagnostische Möglichkeiten, moderne Therapiestrategien; WVG mbH Stuttgart 2003
4. Reisberg B., Ferris S. H., de Leon M. J., Crook T., 1982, The global deterioration scale for assessment of primary degenerative dementia, Am J Psychiatry 139:1136-1139
5. McKhann G., Drachmann D., Folstein M., Katzman R., Price D., Stadlan E. M. 1984, Clinical diagnosis of Alzheimer's disease: Report of the NINCDS-ARDA work group under the auspices of department of health services task force on Alzheimer's disease, Neurology 24: 939-944
6. MCKEITH I. G. (2002). Dementia with lewy bodies. British Journal of Psychiatry 180: 144-147
7. FRANK R. A., GALASKO D., HAMPEL H., HARDY J., DE LEON M. J., MEHTA P. D., ROGERS J., SIEMERS E., TROJANOWSKI J. Q. (2003). Biological markers for therapeutic trials in Alzheimer's disease. Proceedings of the biological markers working group; NIA initiative on neuroimaging in Alzheimer's disease. Neurobiology of Aging 24: 521-536
8. GROWDON J. H., SELKOE D. J., ROSES A., TROJANOWSKI J. Q., DAVIES P., APPEL S. et al. [Working Group Advisory Committee]. (1998). Consensus report of the Working Group on Biological Markers of Alzheimer's Disease. [Ronald und Nancy Reagan Institute of the Alzheimer's Association and National Institute on Aging Working Group on Biological Biomarkers of Alzheimer's Disease]. Neurobiology of Aging 19: 109-116
9. Nils G. Morgenthaler, Joachim Struck, Barbara Thomas, Andreas Bergmann, "Immunoluminometric Assay for the Midregion of Pro-Atrial Natriuretic Peptide in Human Plasma", Clinical Chemistry 50, No. 1, 2004, pages 234-236.
10. TEUNISSEN C. E., DE VENTE J., STEINBUSCH H. W. M., DE BRUIJN C. (2002). Biochemical markers related to Alzheimer's dementia in serum and cerebrospinal fluid. Neurobiology of Aging 23:485-508
11. TARKOWSKI E. (2002). Cytokines in dementias. Current Drug Targets—Inflammation and Allergy 1: 193-200
12. TARKOWSKI E., LILJEROTH A. M., MINTHON L., TARKOWSKI A., WALLIN A., BLENNOW K. (2003). Cerebral pattern of pro- and anti-inflammatory cytokines in dementias. Brain Research Bulletin 61: 255-260
13. CHU D. Q., SMITH D. M., BRAIN S. D. (2001). Studies of the microvascular effects of adrenomedullin and related peptides. Peptides 22:1881-1886
14. Karin Nilsson, Lars Gustavson, Björn Hultberg, Plasma Homocystein Concentration and Its Relation to Symptoms of Vascular Disease in Psychogeriatric Patients, Dement Geriatr Cogn Disord 2005; 20:35-41
15. M. D. Albadalejo, M. Antem, I. Pastor, C. Ruiz, R. Gonzalez-Aniorte, M. Asensio, Determinacion plasmatica de peptidos natriureticosen dementes, Rev Neurol 1997; 25 (139)

The invention claimed is:

1. A method for assisting in the early detection of Alzheimer's disease, the method comprising:
    (a) contacting a blood, plasma or serum sample obtained from a patient in whom Alzheimer's disease (AD) is suspected with first and second antibodies, each of which specifically binds to a peptide consisting of the amino acids sequence PEVPPWTGEVSPAQRDGGALGRGPWDSSDRSALLKSKL (SEQ ID NO: 1), wherein said first and second antibodies bind to a pro-atrial naturiuretic peptide (pro-ANP) peptide comprising the amino acids sequence PEVPPWTGEVSPAQRDGGALGRGPWDSSDRSALLKSKL (SEQ ID NO: 1) in said sample to form labeled immunocomplexes of pro-ANP and first and second antibodies and wherein at least one of said first and second antibodies comprises a detectable label; and
    (b) determining the amount of immunocomplex-associated detectable label in the blood, plasma or serum sample, wherein the amount of detectable label in said sample correlates to the amount of pro-ANP in the sample,
    wherein, if the amount of pro-ANP in said sample is equal to or greater than 87.0 pmol/L, Alzheimer's disease is indicated.

2. The method of claim 1, wherein said patient is suspected of having Alzheimer's disease based on the presence of clinical findings consistent with a diagnosis of AD.

3. The method of claim 2, wherein said patient is asymptomatic for a cardiovascular condition associated with elevated pro-ANP.

4. The method of claim 1, wherein each of said first and second antibodies bind to a separate epitope of the peptide consisting of the amino acid sequence of SEQ ID NO: 1.

* * * * *

SEQUENCE LISTING

<160> NUMBER OF SEQ ID NOS: 1

<210> SEQ ID NO 1
<211> LENGTH: 38
<212> TYPE: PRT
<213> ORGANISM: Homo sapiens

<400> SEQUENCE: 1

Pro Glu Val Pro Pro Trp Thr Gly Glu Val Ser Pro Ala Gln Arg Asp

-continued

```
1               5                   10                  15
Gly Gly Ala Leu Gly Arg Gly Pro Trp Asp Ser Ser Asp Arg Ser Ala
            20                  25                  30
Leu Leu Lys Ser Lys Leu
        35
```